(12) United States Patent
Riede et al.

(10) Patent No.: US 6,384,090 B2
(45) Date of Patent: May 7, 2002

(54) PREPARATION OF ACTIVE INGREDIENT DISPERSIONS AND APPARATUS THEREFOR

(75) Inventors: Thomas Riede, Bensheim; Werner Göbel, Meckenheim; Christian Lockemann, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/726,249

(22) Filed: Nov. 30, 2000

Related U.S. Application Data

(62) Division of application No. 08/944,984, filed on Oct. 7, 1997, now Pat. No. 6,197,836, which is a continuation of application No. 08/544,450, filed on Nov. 17, 1995, now abandoned.

(30) Foreign Application Priority Data

Dec. 19, 1994 (DE) .......................... 44 45 341

(51) Int. Cl.⁷ .......................... B01F 3/12; B01D 11/00; A01N 25/04; A61K 9/107; A61K 9/127
(52) U.S. Cl. .......................... 516/31; 516/9; 516/926; 514/725; 504/362; 424/450; 422/255; 422/281
(58) Field of Search .......................... 516/31, 9, 926; 514/725; 208/952; 422/255, 261, 281; 210/634, 511; 95/187; 504/362; 424/450

(56) References Cited

U.S. PATENT DOCUMENTS

| | | | | |
|---|---|---|---|---|
| 4,898,673 A | * | 2/1990 | Rice et al. | 210/634 |
| 4,962,275 A | * | 10/1990 | Bruno | 210/634 |
| 5,043,280 A | * | 8/1991 | Fischer et al. | 210/634 |
| 5,301,664 A | * | 4/1994 | Sievers et al. | 182/200.23 |
| 5,380,826 A | * | 1/1995 | Castor et al. | 530/422 |
| 5,554,382 A | * | 9/1996 | Castor | 264/4.1 |
| 5,700,482 A | * | 12/1997 | Frederiksen et al. | 264/4.1 |
| 5,704,276 A | * | 1/1998 | Osajima et al. | 99/232.2 |
| 6,197,836 B1 | * | 3/2001 | Riede et al. | 516/31 |

FOREIGN PATENT DOCUMENTS

| | | | |
|---|---|---|---|
| DE | 29 43 267 | * | 10/1979 |
| EP | 322 687 | * | 7/1989 |

OTHER PUBLICATIONS

Translation PTO 97–0381 of DE 2,943,267, (USPTO, Wash., DC, Nov. 1996).*

Database WPI on EAST, week 198120, London: Derwent Publications Ltd., AN—81—34561D [20], DE 29 43 267 A (BASF AG [BADI]) abstract.*

* cited by examiner

Primary Examiner—Daniel S. Metzmaier
(74) Attorney, Agent, or Firm—Keil & Weinkauf

(57) ABSTRACT

The invention relates to a process and an apparatus for preparing active ingredient dispersions, wherein an active ingredient is dissolved in a fluid gas, the fluid gas loaded with active ingredient is essentially completely dissolved in a liquid and is decompressed, and the gas is separated from the liquid loaded with active ingredient.

8 Claims, 4 Drawing Sheets

PREPARATION OF ACTIVE INGREDIENT DISPERSIONS AND APPARATUS THEREFOR

CROSS-REFERENCE TO RELATED APPLICATIONS

This is a Divisional application of application Ser. No. 08/944,984, now U.S. Pat. No. 6,197,836, which was filed on Oct. 07, 1997, as a Continuation application of application Ser. No. 08/544,450, filed Nov. 17, 1995 now abandoned.

The present invention relates to a process and an apparatus for preparing active ingredient dispersions.

BACKGROUND OF THE INVENTION

It is nowadays necessary in many sectors of the chemical industry to prepare active ingredient dispersions, eg. in the color and dye industry and the drugs industry. In this connection it is often impossible to disperse. the active ingredient, eg. the dye or the drug, directly in an aqueous liquid. In particular, the active ingredient particles are then not in the desired micronized form.

The preparation of very finely divided, micronized carotenoids in an aqueous dispersion is described in DE-A 29 43 267. In this case, a carotenoid is dissolved in a supercritical gas in an autoclave, and the resulting solution is dispersed in a suitable aqueous colloidal matrix, which is located in a second autoclave, using an agitator. The resulting dispersion consists of droplets of fluid gas containing active ingredient in water. This two-phase system is decompressed, with the gas being continuously discharged from the autoclave, whereas the liquid can be removed only batchwise after completion of the process. This process results in an average particle size of the carotenoid of less than 1 micron. A disadvantage is that phase separation may occur during the decompression process so that the active ingredient is insufficiently stabilized by the liquid matrix. In addition, a loss of active ingredient must be accepted.

European Patent 0 322 687 proposes a process for preparing a drug form comprising an active ingredient and a carrier. This entails a fluid gas, an active ingredient and carrier materials, which can also be dissolved in a liquid, being introduced into a spray tower so that the fluid gas picks up active ingredient and carrier. The fluid gas is subsequently separated from the resulting active ingredient/ carrier combination in a separator so that the combination can be removed from the separator. This process produces dry active ingredient particles but not liquid dispersions. Fluid gas means a substance which is in the form of a gas or vapor under atmospheric pressure and which has been compressed to the vicinity of its critical point or beyond and is therefore in the form of a sub- or supercritical fluid.

SUMMARY OF THE INVENTION

It is an object of the present invention to provide a process and an apparatus for preparing active ingredient dispersions which lead to a particularly fine dispersion of the active ingredient in the dispersion. In particular, the micronized active ingredients must not agglomerate.

We have found that this object is achieved by the process described herein. This entails an active ingredient being dissolved in a fluid gas, and the fluid gas loaded with active ingredient being finely dispersed in a liquid and, during this, essentially completely dissolved. The solid is formed during the dissolving process of the fluid gas. Each of the individual, finely distributed gas bubbles contains only little solid, so that the solid particles produced therein are very small. Since the particles pass directly into the liquid, where they are preferably bound into protective colloids, and previously only little solid is contained in each of the individual, finely distributed gas bubbles, agglomeration can be virtually ruled out. The solution is then decompressed, and the gas is thus separated from the liquid loaded with active ingredient. Part of the removed liquid loaded with active ingredient is preferably reused as dissolving liquid for the fluid gas. It is possible in this way to achieve a high concentration of the micro-particles in the dispersion, irrespective of the solubility of the active ingredient in the fluid gas. Another preferred process is one in which the solution is not on decompression completely decompressed to atmospheric pressure so that the reused liquid loaded with active ingredient is preloaded with the fluid gas. It is possible in this way to influence both the rate of formation of the solid particles and the morphology thereof. Furthermore, the complete dissolving of the gas in the liquid ensures that the active ingredient passes completely from the gas into the liquid. The process can be carried out continuously or batchwise, and in both cases there is no, or only negligible, agglomeration of particles, preferably because of the stabilization by protective colloids.

The object is also achieved by a process in which an active ingredient is dissolved in a fluid gas, and the fluid gas loaded with active ingredient is dispersed in a liquid saturated with this gas, so that a first dispersion of liquid and fluid gas loaded with active ingredient is formed. The active ingredient is in this case transferred to the phase boundary by molecular diffusion from the gas. The solid then forms only at the phase boundary and passes from there directly into the liquid, where it is immediately stabilized, preferably by protective colloids, so that agglomeration is ruled out. This first dispersion is passed through a holdup section to form a second dispersion of liquid loaded with active ingredient and fluid gas. The second dispersion is then separated, without previous decompression, by phase separation into a gas phase and a third dispersion of liquid and active ingredient. Part of the third dispersion is finally reused to form the first dispersion with the fluid gas. It is advantageous that a large part of the gas can be reused for dissolving the active ingredient without renewed compression.

In another embodiment, an active ingredient is dissolved in a fluid gas, and the fluid gas loaded with active ingredient is decompressed to form a first dispersion of gas and active ingredient. This first dispersion is dispersed in a liquid to give a second dispersion which is passed through a holdup section and separated into a gas phase and a third dispersion of liquid and active ingredient. Preferably part of the third dispersion which has been separated off is reused as liquid to form the second dispersion.

It is preferred to recycle the gas which has been separated off and is reused as fluid gas for dissolving the active ingredient. The active ingredient used preferably consists of a mixture of a plurality of active ingredients. Preferred active ingredients are dyes, vitamins, carotenoids, polymers, liposomes, drugs or crop protection agents. Preferred fluid gases are $CO_2$, $N_2O$, ethylene, propane, $H_2O$, $NH_3$, hydrocarbons, alcohols and mixtures of these substances The preferred liquid used is water or an organic solvent which is preferably supplemented with additions of protective colloids such as surfactants, polymers, celluloses, dextrins or proteins such as gelatin and/or emulsifiers or the like.

The object of the invention is also achieved by the apparatus described herein. An apparatus according to the apparatus claims comprises an extractor for dissolving an active ingredient in a fluid gas, which is connected via a line to a mixer for dissolving the fluid gas loaded with active ingredient in a liquid. The liquid is fed to the mixer through another line. The apparatus additionally contains a holdup section which is connected to a separator in which the gas is separated from the liquid containing active ingredient. The separator has discharge lines for the gas which has been separated off and for the liquid which has been separated off. The apparatus additionally contains a return feed for part of the liquid which has been separated off to the mixer.

A decompression valve is preferably fitted between the holdup section and the separator. In a preferred embodiment, the discharge line for the gas which has been separated off returns the latter from the separator to the extractor.

BRIEF DESCRIPTION OF THE DRAWINGS

The invention is described hereinafter by means of FIGS. 1 to 4. In these.

DESCRIPTION OF THE PREFERRED EMBODIMENTS

Figure 1:
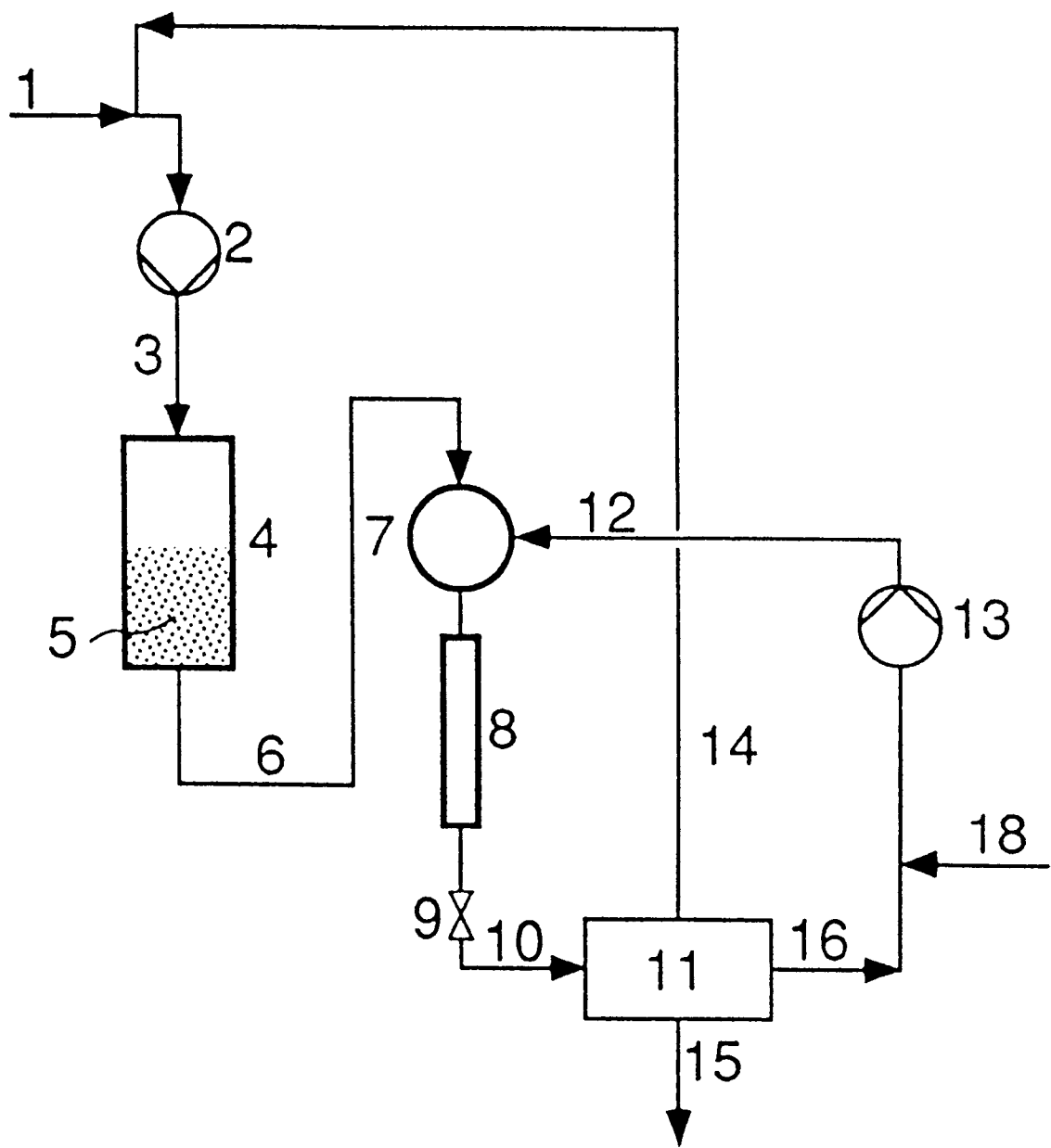
FIG. 1 shows experimental design for a first variant of the process.

In FIG. 1, a gas 1 is converted with the aid of a compressor 2 into the supercritical, ie. fluid, state. This fluid gas 3 takes up the active ingredient 5 in an extractor 4. The fluid gas loaded with active ingredient is then fed through line 6 to the mixer 7 where it is mixed with a liquid which is fed through line 12 to the mixer. The fluid gas loaded with active ingredient is essentially completely dissolved in the liquid in the mixer 7 and the subsequent holdup section 8. The active ingredient dissolved in the fluid gas precipitates in the form of very finely dispersed particles with sizes in the range below 1 μm into the liquid. The resulting active ingredient/liquid dispersion is decompressed through valve 9 and fed through line 10 to the separator 11. Part of the liquid loaded with active ingredient is discharged through line 15, and the other part is passed through line 16 and compressor 13 together with fresh liquid, which is supplied by line 18, through line 12 to the mixer 7. This partial recycling makes it possible to determine the concentration of active ingredient particles in the dispersion, irrespective of the solubility of active ingredient in the fluid gas. The gas which has been separated off is discharged through line 14 and returned to the circulation upstream of the compressor 2. The solution can be completely decompressed, or else decompressed to a pressure above atmospheric pressure, at the end of the holdup section.

Figure 2:
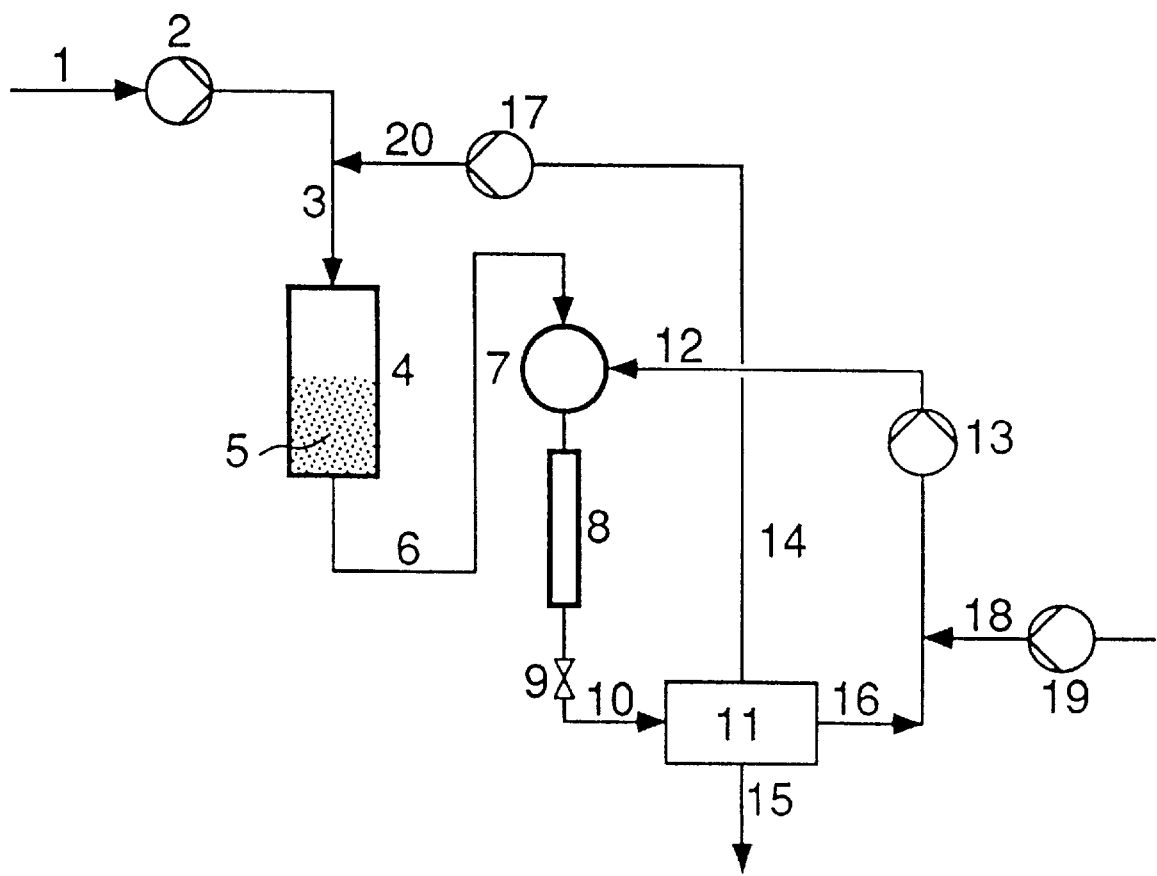
FIG. 2 shows experimental design for a second variant of the process.

An incomplete decompression, as depicted in FIG. 2, results in the liquid being preloaded with fluid gas, by which means it is possible to influence the crystallization rate in the formation of the active ingredient particles, just like their morphology. The recycling of the gas takes place in this case by the gas which has been separated off being discharged through line 14, compressed to the pressure of the system in the decompressor 17 and returned to the circulation through line 20 downstream of the compressor 2. Fresh liquid is compressed in the compressor 19 and fed to the circulation through line 18.

Figure 3:
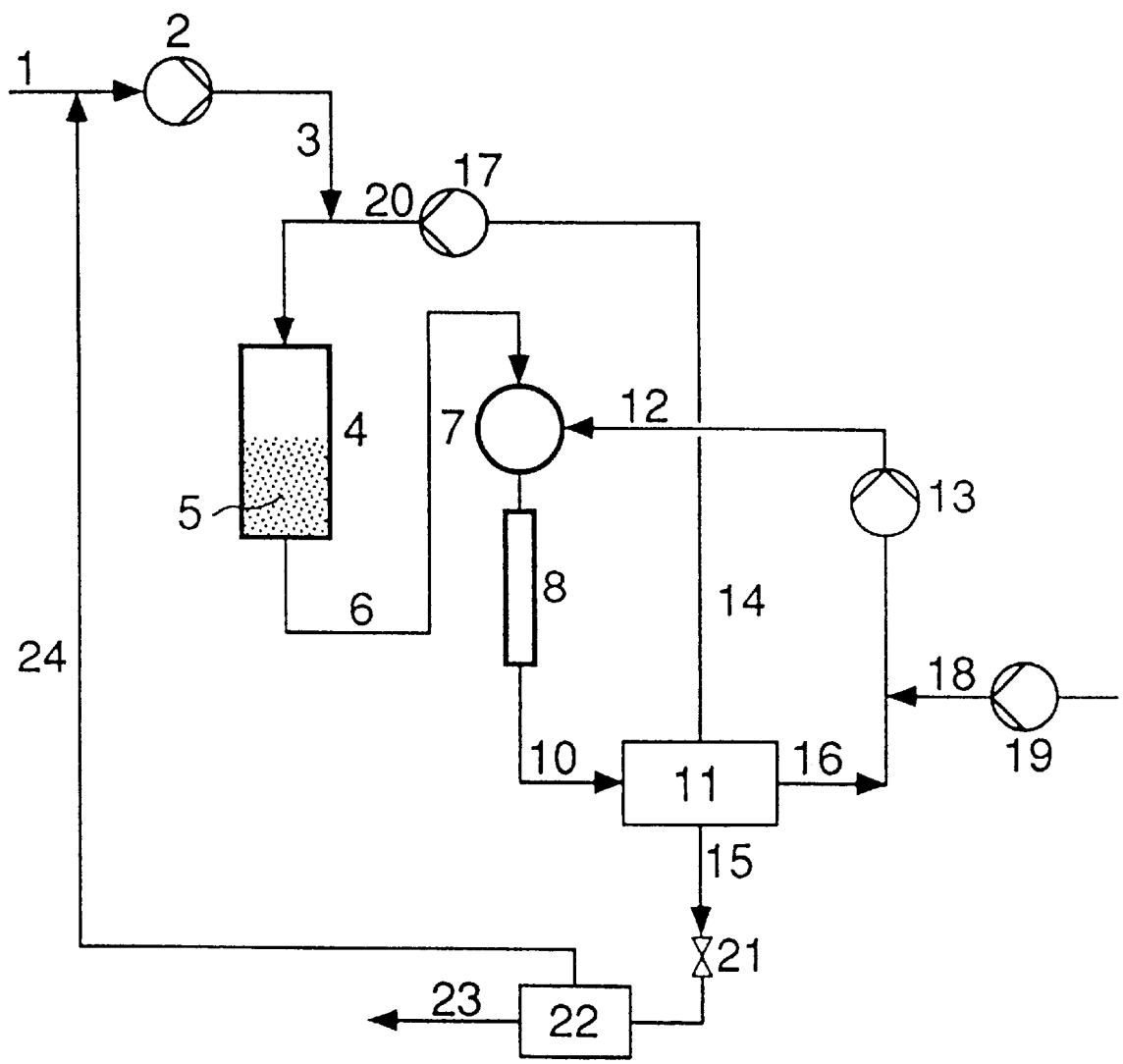
FIG. 3 shows experimental design for a third variant of the process.

In the variant of the process which is depicted in FIG. 3, the fluid gas is likewise fed to the extractor 4 with the active ingredient 5 and reaches, as fluid gas loaded with active ingredient, the mixer 7. However, the fluid gas does not dissolve in the liquid in the mixer and the subsequent holdup section 8, on the contrary the fluid gas loaded with active ingredient is dispersed with a liquid, which is supplied through line 12 and which is saturated with the same gas. The active ingredient dissolved in the fluid gas diffuses to the phase boundary, precipitates there in the form of microparticles and is then bound in the liquid, preferably by protective colloids. The second dispersion, which is now produced, of liquid loaded with active ingredient and of fluid gas is not decompressed but is directly fed to a separator 11. Part of the liquid loaded with active ingredient is removed through discharge line 15, which is provided with a decompression valve 21. This solution is separated from dissolved gas in the separator 22 and discharged through line 23. The gas is returned again via line 24 upstream of the compressor 2. The other part of the liquid loaded with active ingredient is discharged through line 16 out of the separator, supplemented with fresh liquid through line 18 and compressor 19 and circulated by the circulating pump 13, which compensates the pressure drop in the lines. The liquid is then fed through line 12 to the mixer 7 again. The fluid gas which has been separated off is returned through line 14, circulating pump 17 and line 20 to the extractor 4.

Figure 4:
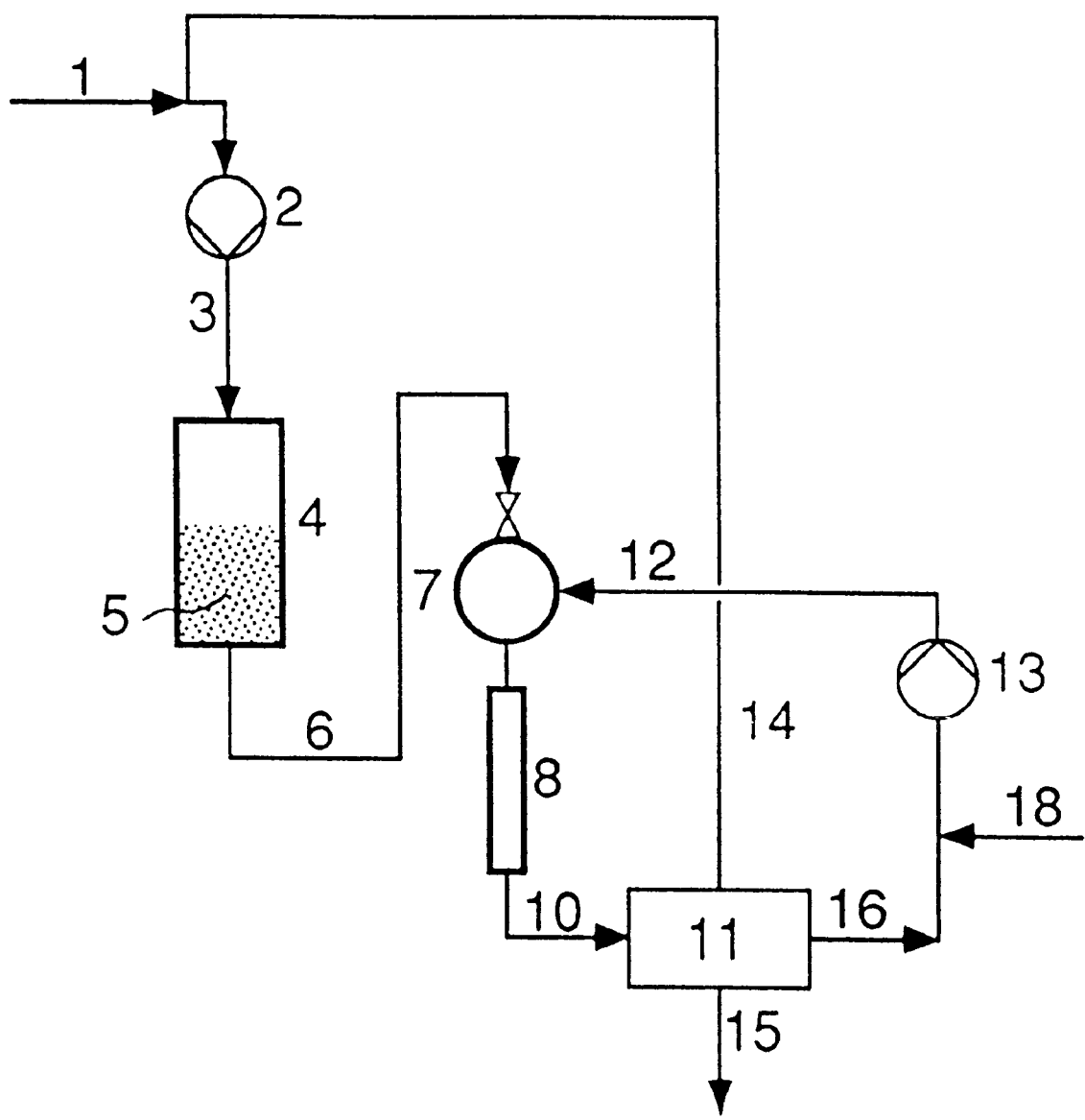
FIG. 4 shows experimental design for a fourth variant of the process.

In the variant of the process shown in FIG. 4, the fluid gas loaded with active ingredient is mixed in the mixer 7 with a liquid supplied through line 12 and, at the same time, decompressed. The fluid gas containing active ingredient is thus present in the form of gas bubbles in the liquid. The active ingredient particles diffuse at the phase boundary of the gas bubbles into the liquid. The resulting dispersion is then separated in the separator 11 into a gas phase and a third dispersion of liquid and active ingredient. The liquid loaded with active ingredient is in turn discharged through discharge lines 15 and 16 or compressed in the compressor and returned to the mixer. The gas which has been separated off is returned upstream of the compressor 2 for reuse as fluid gas.

EXAMPLE 1

About 5 g of β-carotene were introduced into a temperature-controllable autoclave with a capacity of 250 ml. An $N_2O$ stream (250 bar–0.8 kg per hour) was preheated to 45° C. and passed into the autoclave. The $N_2O$ stream loaded with carotene was then fed through a thermostated line to a mixing nozzle. The gas stream was there dispersed in an aqueous solution which contained 3.8% by weight of gelatin. During this the temperature was 45° C. and the pressure was 250 bar. The dispersion subsequently passed through a holdup section where the gas completely dissolved in the aqueous solution. Finally, the dispersion was decompressed in a separator, and the desorbed gas was separated from the solution. The liquid was subsequently compressed again to 250 bar and returned to the mixing nozzle. The particle size of the carotene contained in the final product was distinctly below 1 μm.

EXAMPLE 2

As in Example 1, about 5 g of β-carotene were introduced into an autoclave. An $N_2O$ stream (45° C., 250 bar, 0.8 kg per hour) was passed through the autoclave; the gas load dispersed as in Example 1 in an aqueous solution which contained 3.8% by weight of gelatin. No decompression took place. After intimate mixing of the compressed gas with the aqueous solution in the holdup section, the compressed gas was separated off in a phase separator. The aqueous solution was conveyed back to the mixing nozzle. Since no decompression took place, the circulated liquid was always saturated with $N_2O$, so that the compressed gas was unable to dissolve in the aqueous solution. Samples of the aqueous solution taken from the circulation and thereby decompressed consisted of a dispersion of carotene particles which particle size was distinctly below 1 µm.

EXAMPLE 3

An $N_2O$ stream loaded with β-carotene was produced as in the preceding examples. This was decompressed through a mixing nozzle into an aqueous solution which was conveyed under atmospheric pressure at 700 l per hour and contained 3.8% by weight of gelatin. The resulting dispersion was subsequently separated in a separator into a gas phase and a liquid loaded with active ingredient. The liquid phase, which assumed a yellow-orange color, was returned to the mixing nozzle. The particle size of the carotene dispersed therein was once again below 1 µm.

We claim:

1. A process for preparing an active ingredient dispersion which comprises:
   i) dissolving an active ingredient in a supercritical fluid gas to form a supercritical fluid gas solution of the active ingredient,
   ii) dispersing the supercritical fluid gas solution of the active ingredient in a gas-saturated liquid to form a first dispersion of the liquid and the supercritical fluid gas solution, wherein the gas saturating the liquid is the same as the gas utilized in supercritical fluid form for dissolving the active ingredient,
   iii) passing the first dispersion through a holdup section to form a second dispersion of the liquid comprising the active ingredient and the supercritical fluid gas,
   iv) separating the second dispersion without previous decompression into the gas phase and a third dispersion of the liquid and the active ingredient, and
   v) recycling a part of the third dispersion to step (ii).

2. The process of claim 1, wherein the gas phase formed in step (iv) is condensed and recycled into step (i) as the supercritical fluid gas.

3. The process of claim 1, wherein the active ingredient consists of a mixture of a plurality of active ingredients.

4. The process of claim 3, wherein the plurality of active ingredients is selected from the group consisting of dyes, vitamins, carotenoids, polymers, liposomes, drugs, crop protection agents, proteins and peptides.

5. The process of claim 1, wherein the active ingredient is selected from the group consisting of dyes, vitamins, carotenoids, polymers, liposomes, drugs, crop protection agents, proteins and peptides.

6. The process of claim 1, wherein the supercritical fluid gas is selected from the group consisting of fluid $CO_2$, $N_2O$, ethylene, propane, $H_2O$, $NH_3$, hydrocarbons, alcohols and mixtures thereof.

7. The process of claim 1, wherein the liquid is water or an organic solvent, optionally in mixture with surfactants, polymers, celluloses, dextrins, proteins and/or emulsifiers.

8. The process of claim 7, wherein the liquid is water or an organic solvent in mixture with gelatin and optionally further with other proteins, surfactants, polymers, celluloses, dextrins and/or emulsifiers.

* * * * *